United States Patent [19]
Haralampu et al.

[11] Patent Number: 5,849,090
[45] Date of Patent: *Dec. 15, 1998

[54] GRANULAR RESISTANT STARCH AND METHOD OF MAKING

[75] Inventors: Stephen G. Haralampu, Plymouth; Akiva Gross, Newton, both of Mass.

[73] Assignee: Opta Food Ingredients, Inc., Bedford, Mass.

[*] Notice: This patent issued on a continued prosecution application filed under 37 CFR 1.53(d), and is subject to the twenty year patent term provisions of 35 U.S.C. 154(a)(2).

[21] Appl. No.: 622,844

[22] Filed: Mar. 27, 1996

[51] Int. Cl.$^6$ ............................ C08B 30/00; C08B 30/12; A23L 1/05
[52] U.S. Cl. ................................ 127/65; 127/32; 127/67; 127/69; 127/71; 426/661
[58] Field of Search .................................. 127/65, 67, 69, 127/71, 32; 426/661

[56] References Cited

U.S. PATENT DOCUMENTS

| | | | |
|---|---|---|---|
| 3,556,942 | 1/1971 | Hathaway | 127/65 |
| 5,051,271 | 9/1991 | Iyengar et al. | 426/658 |
| 5,089,171 | 2/1992 | Chiu et al. | 252/315.3 |
| 5,194,284 | 3/1993 | Chiu et al. | 426/589 |
| 5,281,276 | 1/1994 | Chiu et al. | 127/65 |
| 5,409,542 | 4/1995 | Henley et al. | 127/65 |
| 5,468,286 | 11/1995 | Wai-Chiu et al. | 106/210 |
| 5,593,503 | 1/1997 | Shi et al. | 127/71 |

FOREIGN PATENT DOCUMENTS

| | | | |
|---|---|---|---|
| 564893A1 | 10/1993 | European Pat. Off. | C12P 19/16 |
| 616779A1 | 9/1994 | European Pat. Off. | A23L 1/09 |
| 688872A1 | 12/1995 | European Pat. Off. | |
| 747397A2 | 12/1996 | European Pat. Off. | C08B 30/12 |
| 91/07106 | 5/1991 | WIPO | A23L 1/308 |
| 92/21703 | 12/1992 | WIPO | C08B 30/00 |
| 94/14342 | 7/1994 | WIPO | A23L 1/308 |
| 95/04082 | 2/1995 | WIPO | C08B 30/12 |

OTHER PUBLICATIONS

Jane and Robyt, "Structure Studies of Amylose–V Complexes and Retrograded Amylose by Action of Alpha Amylases, and a New Method for Preparing Amylodextrins", *Carbohydrate Research* 132:105–118.

Englyst and Cummings, "Digestion of the Polysaccharides of Some Cereal Foods in the Human Small Intestine", *Am. J. Clin. Nutr.* 42:778–787 (Nov. 1985).

Annison and Topping "Nutritional Role of Resistant Starch: Chemical Structure vs Physiological Function" *Annu. Rev. Nutr.* 14:297–320 (1994) month n/a.

Garcia et al., *Starch* 49:171–179 (1997) [(Exhibit A of an amdt. filed Jul. 16, 1997)].

*Primary Examiner*—Deborah Jones
*Assistant Examiner*—Patricia L. Hailey
*Attorney, Agent, or Firm*—Hamilton, Brook, Smith & Reynolds, P.C.

[57] ABSTRACT

A method of producing a granular resistant starch comprising the steps of heating a granular native starch to swell but not rupture the starch granules, debranching the starch, treating the starch to retrograde the amylose therein, optionally annealing the starch and optionally drying the product to a powder is described. Granular resistant starch produced by this method and food formulations containing the granular resistant starch are also described.

24 Claims, No Drawings

GRANULAR RESISTANT STARCH AND METHOD OF MAKING

BACKGROUND OF THE INVENTION

Resistant starch is the portion of starch which, due to physical constraints, is poorly hydrolyzed by amylases. Some of the conditions which limit enzymatic hydrolysis are physical entrapment in a non-digestible matrix, crystallinity due to structure in ungelatinized starch granules which may be destroyed at relatively low temperatures and crystallinity due to retrogradation which is considerably more stable. The resistance of starches has been investigated by a number of researchers (e.g., Jane and Robyt, *Carbohydrate Research* 132:105–118 (1984); Englyst and Cummings, *Am. J. Clin. Nutr.* 42:778–787 (1985); and Annison and Topping, *Annu. Rev. Nutr.* 14:297–320 (1994)).

One feature of resistant starch is that it interferes with the traditional measurement of total dietary fiber by the Prosky method (Englyst et al., *Analyst* 107:307–318 (1982)), which has generated considerable controversy. Since the classical definition of fiber is non-starch polysaccharide, resistant starch should not be considered fiber by the classical definition. However, nutritional studies show that resistant starch possesses some of the physiological benefits of fiber, and should be properly considered as a fiber. Some benefits cited include increased fecal bulk, lowered fecal pH, increased excretion of butyrate and acetate (Phillips et al., *Am. J. Clin. Nutr.* 62:121–130 (1995)), increased ilial crypt cell production rate (Gee et al., *J. Nutr.* 121:44–49 (1991)), and decreased serum triacylglycerol concentration (DeDeckere et al., *Br. J. Nutr.* 73:287–298 (1995)). These benefits are primarily seen in soluble dietary fibers.

In addition to utility as a fiber constituent, the slow hydrolysis of resistant starch makes it useful for the slow release of glucose, which can be especially useful in controlling glycemic plasma responses (Raben et al., *Am. J. Clin. Nutr.* 60:544–511 (1994)). U.S. Pat. No. 5,470,839 (Laughlin et al.) teaches the use of raw high amylose starch as a source of resistant starch useful for foods for diabetics.

Methods for producing resistant starch products disclosed in U.S. Pat. Nos. 5,051,271 (Iyengar et al.) and 5,409,542 (Henley et al.) utilize the steps of fully hydrating and cooking a starch, preferably a high amylose hybrid, optionally enzymatically debranching the amylopectin therein, and incubating the mixture under conditions to retrograde the amylose to yield resistant starch. One disadvantage of these methods is that full hydration and cooking of the starch produces mixtures with very high viscosities during the retrogradation. High viscosities are managed by running at low concentration, which is inefficient and results in excessive drying costs when producing a powdered ingredient.

SUMMARY OF THE INVENTION

The present invention pertains to a method of making granular resistant starch comprising heating a granular native starch to cause the native starch granules to swell but not rupture, debranching the swollen native starch, treating the debranched, granular starch to retrograde the amylose, and optionally annealing the starch, thereby producing granular resistant starch. The invention also relates to granular resistant starch produced by the process described herein, and food formulations comprising the granular resistant starch.

In one embodiment of the invention, an aqueous slurry of a granular native starch is heated (e.g., with a batch tank heater or heating plate) to a temperature sufficient to swell the native starch granules without disrupting the starch granules. The swelled granular native starch is then treated with a debranching enzyme (e.g., pullulanase) under conditions appropriate to substantially or totally debranch the amylopectin present in the starch. The debranched granular starch is treated under thermal conditions sufficient to retrograde the amylose. The product of the described process can be cooled to form an aqueous granular resistant starch slurry having a lower viscosity than resistant starches produced by traditional processes. The aqueous slurry can optionally be dried (e.g., by spray drying) to a powder. The granular resistant starch will have a total dietary fiber (TDF) content of from about 20% to about 50% by weight.

In another embodiment of the invention, the retrograded starch can optionally be annealed. Annealing promotes perfection of order in the starch structures and enhances the yield of thermally stable retrograded starch as measured by differential scanning calorimetry (DSC) peak enthalpy, resistant starch or percent TDF. Annealing can be accomplished by oscillating the temperature between a temperature just below the melting point of the starch and a temperature just above the glass transition temperature. Alternatively, the temperature can be maintained just below the melting point of the starch for a time sufficient to anneal the starch. The annealing step can be carried out concurrently with or after the retrogradation step. In a particular embodiment, the annealing cycle is carried out more than once. The product of the described annealing process can be cooled to form an aqueous granular resistant starch slurry having a lower viscosity than resistant starches produced by prior art methods. The aqueous slurry can optionally be dried (e.g., by spray drying) to a powder.

The granular resistant starch can also be optionally co-processed with hydrocolloids, polymers, gums, modified starches and combinations thereof, which additional ingredients can be added to change the functional properties of the granular resistant starch. For example, the granular resistant starch can be co-processed with dispersion aids, such as maltodextrin, or hydrocolloids, which can assist in altering the functional properties of the composition such as viscosity building and water binding.

The granular resistant starch produced by the described process is characterized by TDF values in the range of from about 20% to about 50% by weight. The aqueous granular resistant starch slurry will have a lower viscosity than resistant starch slurries produced by traditional processes of the prior art. In the present invention, it is preferable to form thermally stable retrograded amylose (thermally stable resistant starch) with a DSC peak above about 125° C., as such starch is sufficiently thermally stable to survive most cooking processes.

The granular resistant starch produced by the methods described herein is useful in a variety of food and beverage applications. Foods and beverages which can be formulated with the granular resistant starch of the present invention include cookies, breads, cakes, pies, noodles, fudge, brownies, low-fat margarine, snack dips, sour cream, mayonnaise, cream cheese and other spreads, yogurt, milkshakes, ice cream and frozen desserts. The granular resistant starch can also be included in snack item formulations such as crackers, graham crackers, pretzels and similar products, as well as in extruded foods such as extruded snacks and cereals.

By maintaining the starch granule integrity, the method of making a granular resistant starch composition described herein has the advantage of producing a composition with a significant percent of total dietary fiber while avoiding the extremely high viscosities encountered during retrogradation in traditional resistant starch processes. The high viscosities produced during starch retrogradation in prior methods requires that the process be run at low concentrations, which is inefficient and results in excessive drying costs when producing a powdered composition. One advantage of the present invention is that thermally stable granular resistant starch can be efficiently produced with reduced process complexity due to the increased concentrations which can be utilized.

DETAILED DESCRIPTION OF THE INVENTION

The invention relates to a method of making granular resistant starch by heating a granular native starch under conditions sufficient to swell the starch granules, subsequently debranching the amylopectin present in the starch, and treating the granular debranched starch under conditions sufficient to retrograde the amylose and, optionally, anneal the starch. The granular resistant starch produced by the described process can be utilized in the form of an aqueous dispersion or can be dried to a powder. The powder can optionally be redispersed in an aqueous medium with medium shear.

Any native or pregelatinized starch can be used as the starting material of the present invention as long as the starch granules therein are intact. Particularly preferred starches are high amylose starches, most preferably starches containing at least 30% amylose, when measured by iodine binding (Schoch, T. J., *Methods in Carbohydrate Chemistry* 4:157–160 (1964)). Suitable starches include corn, potato, wheat, rice, barley, tapioca, cassava, arrow-root, sago and oat starches. For example, a hybrid of corn starch, such as starch from the ae7 hybrid of corn, available under the trade names AMYLOMAIZE VII® (American Maize Products Company, Hammond, Ind.) and HYLON VII® (National Starch and Chemical Company, Bridgewater, N.J.), is a particularly suitable starch. This starch will assay to less than about 20% TDF (total dietary fiber) and when analyzed by differential scanning calorimetry (DSC) exhibits thermal activity peak (gelatinization) from about 55° C. to 130° C. with a peak at about 95° C. and total peak enthalpy of about 24 J/g. The product of this invention assays from about 20% to about 50% TDF by weight and is shown to be more thermally stable when analyzed by DSC since it exhibits thermal activity from about 90° C. to 150° C. with a peak at about 125° C. Thus, since the thermal activity is higher than normal cooking temperatures, resistance is preserved in most food processes.

The granular native starch is combined with an aqueous medium such as water or a buffer to produce a slurry; the aqueous medium can also be a mixed organic solvent (such as a mixture of water and alcohol), depending upon the desired end product. Generally, food grade aqueous media should be used if the ultimate use is a food or beverage product. The dispersion or slurry generally contains from about 1% to about 50% (w/w) of starch. The slurry is then heated under conditions sufficient to swell the native starch granules present in the slurry without rupturing the starch granules. That is, under heating conditions appropriate for this step of the invention, the granular structure of the starch is not disrupted, and the starch granules, although swollen, remain intact.

Swelling the starch granule hydrates the starch molecules, presumably making them accessible for subsequent debranching and making them sufficiently mobile to retrograde into thermally stable resistant starch with a DSC peak at about 125° C. By maintaining some granule integrity, however, the extremely high viscosities encountered during retrogradation in traditional resistant starch processes are significantly lowered.

Generally, temperatures considered appropriate for the present invention range from about 60° C. to about 120° C., with from about 70° C. to about 100° C. being particularly preferred. For example, in the case of AMYLOMAIZE VII® (73% amylose corn starch), temperatures sufficient to swell the granules without disrupting them are from about 60° C. to about 100° C., and preferably from about 75° C. to about 90° C. The type of heating equipment is not critical, and heating may be accomplished by a jacketed reactor, heat exchanger, extruder or direct steam injection. Generally, the time required to sufficiently swell the starch granules will be less than about 2 hours, with less than about 1 hour being preferred, depending upon the starch used.

In some cases, a small amount of amylose leaches from the starch granules during the swelling process, building viscosity during the retrogradation part of the process. This phenomenon can be controlled by regulating the time and temperature conditions used to swell the starch granules and depends upon the type of starch used as a starting material. For instance, the time and/or temperature of the swelling step can be reduced to minimize amylose leakage.

Since the retrogradation of amylose is retarded by the presence of amylopectin in the starch, once the starch granules have been sufficiently swollen, the starch is treated to release short chain amylose. Generally, release of the short chain amylose from the starch will be carried out by enzymatically debranching the starch, e.g., the starch can be debranched with α-1,6-specific glycosidic enzymes which are capable of cleaving α-1,6-D-glucosidic linkages. For instance, the starch can be treated with an isoamylase or with a pullulanase at a temperature and pH and for a time sufficient to allow the enzyme to release the short chain amylose; often, appropriate reaction conditions will be suggested by the manufacturer. A suitable pullulanase can be purchased commercially under the trade name PROMOZYME® 200L (Novo Nordisk Biochem North America, Inc., Franklinton, N.C.).

Generally, appropriate temperatures will range from about 25° C. to about 100° C., with from about 55° C. to about 65° C. being preferred, for a time of from about half an hour to about 30 hours, with from about half an hour to about 4 hours being particularly preferred, depending on the enzyme utilized, the enzyme concentration, and the starting material. Furthermore, the pH of the solution as is optimal for enzyme activity will be from about 3 to about 7.5. In a particularly preferred method, the granular starch is treated with pullulanase at 60° C. at pH 5 for about 4 hours. The optimum conditions for the enzymatic reaction will vary, with changes in parameters such as starch and enzyme concentrations, pH, temperature and other factors readily determinable by the skilled artisan.

Alternatively, the starch can be randomly hydrolyzed and debranched by use of an appropriate acid, such as a mineral acid or organic acid; generally acid hydrolysis will take place at a pH of less that about 4 and at a temperature greater than about 60° C. but less than the gelatinization temperature of the particular starch used, depending upon the acid used. The conditions for acid hydrolysis should be such that inappropriate side reactions are minimized and the starch granules remain intact. Short chain amylose can also be generated by treating the starch with an alpha amylase, alone or in combination with pullulanase.

Without wishing to be bound by theory, debranching presumably enhances the described process by increasing the relative concentration of straight chain molecules, or by removing the inhibitory effects of amylopectin on the retrogradation of amylose.

After the starch is substantially or totally debranched, the debranched granular starch is treated under conditions sufficient to retrograde the amylose, thereby forming crystalline regions in the starch molecule interspersed with amorphous regions. Preferably, the resulting granular resistant starch has a TDF value of from about 20% to about 50%.

As defined herein, thermally stable resistant starch is a resistant starch which exhibits most of its thermal activity above 100° C., and is generally derived from retrograded amylose. In the present invention, it is preferable to form thermally stable retrograded amylose (thermally stable resistant starch) with DSC peak above about 125° C. Generally, retrogradation is accomplished by incubating an aqueous mixture of the debranched granular starch at temperatures ranging from about 1° C. to about 120° C. for sufficient time to allow retrogradation to proceed maximally; appropriate times range from about 4 hours to about 100 hours, with from about 4 hours to about 24 hours particularly preferred, depending upon the starch and temperature conditions. To minimize viscosity build-up, elevated temperatures during retrogradation are preferred in the range of from about 60° C. to about 120° C., and from about 70° C. to about 100° C. is most preferred as being the temperature range which both allows retrogradation to proceed at a suitable rate, while keeping process viscosities manageable. Temperatures within the disclosed ranges also serve to inactivate the remaining debranching enzyme.

Annealing may also be optionally introduced into the process. Annealing promotes perfection of order in the starch structures, and enhances the yield of retrograded starch as measured by DSC peak enthalpy, resistant starch or TDF. Annealing may be carried out after the granular starch is debranched; that is, annealing can take place concurrently with or after the retrogradation step. In an annealing process, temperatures are oscillated in the range of 1° C. to 120° C., and preferably in the range of 50° C. to 90° C. Relatively short times at 90° C., on the order of 1 hour, with slow cooling, on the order of about 4 hours, to about 50° C., with a subsequent hold at about 50° C. for about 4 hours comprise a single cycle of the preferred annealing process. Preferably, the annealing cycle is carried out more than once, with two to four annealing cycles being particularly preferred. Alternatively, the granular resistant starch product can be maintained at a temperature slightly below the melting point of the starch for a time of from about 4 hours to about 100 hours.

The product which results if the annealing step is performed is similar to the product obtained if this step is not carried out, except that the product of the annealing step may have increased TDF values and a more sharply defined peak measured by DSC. Regardless of whether the annealing step is carried out or not, the aqueous granular resistant starch can be used in its aqueous form or can be dried to a powder by a number of art-recognized methods, including spray drying, belt drying, freeze drying, drum drying or flash drying. The powder can be stored at room temperature, and can be redispersed in water or another aqueous medium, preferably an aqueous medium which is appropriate for use in food and beverage formulations, under conditions of medium shear. The granular resistant starch of the present invention can be used in food formulations in either form (e.g., aqueous or powder), depending upon the food formulation.

The granular resistant starch can also be co-processed with hydrocolloids, gums, polymers, modified starches and combinations thereof to change the functional properties of the product. For example, xanthan, alginate, carrageenan, carboxymethyl cellulose, methyl cellulose, guar gum, gum arabic, locust bean gum and combinations thereof can be added to the starch at any time during the preparation process, provided that the additional ingredient(s) does not prevent the swelling of the starch granule, the debranching of the amylopectin or the retrogradation of the amylose. That is, these additional ingredients can be heated along with the starting native starch, added prior to or after the debranching step, added to the aqueous slurry of granular resistant starch or dry blended with the powdered composition after drying. Preferably the hydrocolloid, gum, modified starch or polymer is added to the aqueous granular starch slurry prior just prior to drying.

The granular resistant starch produced by the present invention assays as dietary fiber by the Prosky method. The granular resistant starch has a microcrystalline structure and a wide range of water-holding capacities and digestibility. It can be used as a dietary fiber supplement, as a replacement or substitute for sugar and flour in a variety of baked goods, as a fat extender in reduced fat, low-fat and fat free formulations, as a tabletting aid and as an inhibitor of excessive ice crystal formation in frozen products.

The granular resistant starch of the present invention is particularly useful in formulating foods and beverages containing reduced amounts of sugar, flour or fat. Generally, the granular resistant starch will be present in food formulation in amounts ranging from about 1% to about 15%. Foods formulated with the composition of the present invention in place of sugar, flour and/or fat have a lower calorie content, a higher fiber content and/or a lower fat content. Foods and beverages which can be formulated with the granular resistant starch of the present invention include cookies, breads, cakes, pies, noodles, fudge, brownies, low-fat margarine, snack dips, sour cream, mayonnaise, cream cheese and other spreads, yogurt, milkshakes, ice cream and frozen desserts. The granular resistant starch can also be included in snack item formulations such as crackers, graham crackers, pretzels and similar products, as well as extruded foods such as extruded cereals and snacks. The granular resistant starch of the present invention is also suitable for inclusion in nutritional and dietary drinks, as well as in foods for diabetics which are useful for the slow release of glucose. The granular resistant starch of the present invention can be used in sugar-free foods as well; the amount of sugar, flour or fat in a given formulation which can be replaced with the granular resistant starch will depend in part on the formulation, the desired properties of the food and the amount of calorie and/or fat reduction or fiber content desired. The granular resistant starch of the present invention can also be added as an extender to a formulation without reducing any of the other ingredients. The extended product has a lower calorie or fat content per volume compared with the unextended product.

The following Examples are offered for the purpose of illustrating the present invention and are not to be construed to limit the scope of this invention. The teachings of all references cited herein are hereby incorporated herein by reference.

EXAMPLES

Example 1

A slurry of 40 grams HYLON VII® (National Starch and Chemical Company) in 160 ml was prepared and heated to 90° C. on a heating plate, and held covered at 95° C. for 2 hours in an oven. The mixture was cooled to 57° C. and 0.8 ml of PROMOZYME 200L® (Novo Industri, A/S) was added to debranch the starch. Debranching and retrogradation continued at 57° C. for about 3 days.

After debranching, the starch mixture was heated to 90° C. in an incubating oven for about 140 minutes to inactivate the enzyme and anneal the retrograded starch.

The starch mixture was freeze dried. The resultant powder was analyzed for percent total dietary fiber (TDF) using the Prosky Method (AACC Method 32-07), and found to be 29.0% TDF. DSC analysis (Perkin-Elmer, DSC-7) confirmed a retrograded starch peak from 90° C. to 130° C. the effectiveness of the debranching enzyme was confirmed by high performance size-exclusion chromatography (HPSEC) analysis showing a molecular weight (weight average) of 231,000 daltons, in contrast to the starting HYLON VII® at 1,150,000 daltons.

Example 2

A 25% slurry of high amylose corn starch was prepared by blending 35 kg of HYLON VII® and 94.6 liters of water in a scraped-surface, hemispherical bottom, jacketed kettle. The slurry was heated to boiling and maintained at 95° C. to 100° C. for about 1 hour. At this point there was a slight thickening of the starch slurry, indicative of the granules swelling. Next, the slurry was cooled to 57° C. and pH adjusted to 4.9 with dilute phosphoric acid.

Approximately 76 liters of the cooled slurry was debranched with a pullulanase. The enzyme was added at 5% on a starch basis, or 977 ml per 72.3 kg of slurry. The slurry was maintained at 57° C. by tempered water on the vessel jacket and agitated overnight. During this period, the enzyme debranched the amylopectin and the starch retrograded to form the thermally resistant form as quantified by a DSC peak at approximately 125° C.

After the overnight incubation, the slurry was heated to 90° C. for a period of two hours to inactivate the enzyme and to anneal the retrograded starch, as is quantified by better definition of the high temperature DSC peak.

After the two hour annealing period, the starch was dried in a spray dryer. To facilitate atomization, the slurry was diluted with water, maintained at 90° C. and sprayed with a 2-fluid nozzle, using air as the second fluid. Dilution is presumed to be unnecessary for commercial implementation should suitable drying equipment be available.

The resultant powder was analyzed to be 32.6% TDF. DSC analysis confirmed a retrograded starch peak from 99° C. to 147° C. The effectiveness of the debranching enzyme was confirmed by HPSEC analysis showing a molecular weight (weight average) of 292,000 daltons.

Example 3

A 15% high amylose starch slurry was prepared by blending 11 kg of HYLON VII® (National Starch and Chemical Company) and 57 liters of water in a scraped-surface, hemispherical bottom, jacketed kettle. The slurry was heated to about 100° C. over a period of about 50 minutes, and immediately cooled to about 68° C. over a period of about 50 minutes. The pH was 5.0 and did not require adjustment for the debranching enzyme. The debranching enzyme (PROMOZYME 200L®) was added at 3% based on starch, or 340 ml. The enzyme reaction was allowed to proceed for 3 hours, after which the temperature was raised to 90° C., held for 1 hour, and then the temperature was cycled between about 88° C. and about 58° C. to anneal the product. Each thermal cycle consisted of a linear cool lasting 2.8 hours, followed by a 1-hour heating to 88° C. and a 10-minute hold at 88° C. There were a total of four cycles.

The resulting batch was split into two portions. One portion of the batch was spray dried, yielding a white flowable powder. The product assayed as 28% TDF, and had a 20μ median particle size as measured on a Microtrac™ (Leeds and Northrup Instruments, North Wales, Pa.). The resistant starch was confirmed by a DSC peak from 99° C. to 146° C.

The second portion of the batch was co-processed with the hydrocolloid sodium carboxymethyl cellulose (CMC). A 9.5 kg portion of slurry was assayed as 18.3% solid, or containing 1.7 kg of granular resistant starch. The CMC was added on a 10% basis relative to the starch as a 3% aqueous solution. The gum solution was prepared by blending 172 g AQUALON TYPE 7MF® (Hercules Corporation, Wilmington, Del.) and 5.8 liters of water and adding this to the granular resistant starch slurry. This was spray dried, yielding a white flowable powder. The product assayed as 34% TDF and had a median particle size of 20μ as measured on a Microtrac (Leeds and Northrup Instruments, North Wales, Pa.). The higher fiber content reflects the soluble fiber contribution of the CMC. The granular resistant starch was confirmed by a DSC peak from 83° C. to 146° C.

Example 4

A 15% high amylose starch slurry was prepared by blending 11 kg HYLON VII® (National Starch and Chemical Company) and 57 liters of water in a scraped-surface, hemispherical bottom, jacketed kettle. The pH was 5.0 and did not require adjustment for the debranching enzyme. The slurry was heated to about 100° C. over a period of about 40 minutes, and immediately cooled to about 59° C. over a period of about 20 minutes. After heating, the pH had dropped to 4.8. The debranching enzyme (PROMOZYME® 200L) was added at 3% based on starch (dry weight basis) or 306 ml. The enzyme reaction proceeded for 3 hours, after which the temperature was raised to 90° C., held for 1 hour, and then gradually cooled to 55° C. over a 4 hour period and held at 55° C. for an additional 12 hours. The retrograded starch slurry was then spray dried. The granular resistant starch product assayed as 28.7% TDF. Thermally stable resistant starch was confirmed by a DSC peak from about 95° to 145° C., with a minor peak at 107° C. and a broad peak at 120° C.

Example 5

The granular resistant starch of Example 4 was formulated into a yogurt at a level of 1.1% TDF (a level sufficient for a "good source of fiber" by current food regulations). For the 28.7% TDF product of Example 4, this corresponds to a yogurt formulation of:

| Water | 1684 g |
| Non-fat dry milk | 240 g |
| granular resistant starch | 76 g |

The dry ingredients were blended, split in two equal portions, which were then dispersed in 300 ml water in each of two Waring Blenders set on high. The mixtures were blended for 2 minutes. The two portions were combined together and with the remaining water. The mixture was then pasteurized by heating to 91° C. in a double boiler, and transferred to a thermos to stand for 30 minutes. The hot mixture was homogenized in an APV/Gaulin (Everett, Mass.) homogenizer set for 2000 psi in the first stage and 500 psi in the second. The mixture was then cooled to 43° C. and inoculated with 0.026% yogurt culture YC186 (Chr. Hansen, Milwaukee, Wis.). The yogurt was incubated at 43° C. for 6.5 hours before refrigeration at 4° C.

An advisory panel viewed the yogurt as acceptable, with only minor mouth-drying. A fiber assay indicated the yogurt to be 1.43% TDF, 1.18% insoluble fiber and 0.25% soluble fiber. This indicates that the granular resistant starch is sufficiently thermally stable to survive typical food processes like pasteurization and homogenation.

Analytical Methods

DSC Thermal Analysis

Ten milligrams of powdered sample was weighed in a Perkin Elmer high pressure capsule DSC pan. The sample was mixed with 50 μl deionized water and hermetically sealed in the DSC pan. The sample was then analyzed (DSC 7, Perkin-Elmer, Norwalk, Conn.) from 20° C. to 160° C. at 10° C./minute with a sealed empty pan as a reference.

Molecular Weight Distributions

The molecular weight distributions of the debranched samples were analyzed by high performance size-exclusion chromatography (HPSEC). Two Polymer Laboratory (Amherst, Mass.) mixed bed B columns (300×7.5 mm) were connected in series and the temperature of the column maintained at 70° C. The mobile phase was 5 mM sodium nitrate in DMSO at a flow rate of 1 ml/minute. A Waters 400 refractive index detector (Waters Corporation, Milford, Mass.) was used. The columns were calibrated using pullulan standards (Hayashibara Biochemicals, Japan) with molecular weights ranging from 5800 to $1.66 \times 10^4$ daltons and maltose (molecular weight 342 daltons). The molecular weights of the starch samples were obtained using Perkin Elmer's Turbochrome 4 software and the calibration curve for the standards. The starch samples (10 mg) were completely issolved in 4 ml mobile phase by heating at 90° C. in a water bath for 1 hour. A 200 μl sample was injected onto the columns.

Equivalents

Those skilled in the art will recognize, or be able to ascertain, using no more than routine experimentation, many equivalents to the specific embodiments of the invention described herein. Such equivalents are intended to be encompassed by the following claims:

We claim:

1. A method for producing granular resistant starch, comprising the steps of:
   a) heating an aqueous slurry of native starch under conditions appropriate for swelling of the native starch granules therein without causing rupture of said native starch granules;
   b) debranching the starch product of step (a); and
   c) causing the debranched starch product of step (b) to retrograde,
   thereby producing granular resistant starch.
2. A method according to claim 1, wherein step (b) is carried out using a debranching enzyme.
3. A method according to claim 2, wherein the debranching enzyme is pullulanase.
4. A method according to claim 1, wherein the native starch is a high amylose starch.
5. A method according to claim 4, wherein the native starch is derived from corn, potato, wheat, rice, barley, tapioca, cassava, arrow-root, sago and oat starches.
6. A method according to claim 1, further comprising annealing the starch after step (b).
7. A method according to claim 6, further comprising drying the annealed product.
8. A method according to claim 1, further comprising drying the product of step (c).
9. Granular resistant starch produced by the method of claim 1.
10. A food or beverage formulation comprising the granular resistant starch of claim 9.
11. A food or beverage formulation according to claim 10, wherein the food or beverage formulation is selected from the group consisting of cookies, breads, cakes, pies, noodles, fudge, brownies, low-fat margarine, snack dips, sour cream, mayonnaise, cream cheese, spreads, yogurt, milkshakes, ice cream, frozen desserts, crackers, graham crackers, pretzels, extruded cereals and extruded snacks.
12. A food or beverage formulation according to claim 10, wherein the granular resistant starch is present at from about 1% to about 15%.
13. A food or beverage formulation which is a source of slow-released glucose comprising the granular resistant starch of claim 9.
14. A method of producing granular resistant starch, comprising the steps of:
   a) heating an aqueous slurry of native high amylose starch to a temperature of from about 90° C. to about 120° C.;
   b) enzymatically debranching the starch product of step (a); and
   c) heating the debranched starch product of step (b) to a temperature of from about 40° C. to about 100° C. and maintaining the temperature for about 2 hours,
   thereby producing granular resistant starch.
15. A method according to claim 14, further comprising:
   d) altering the temperature of the product of step (c) to achieve a temperature of from about 40° C. to about 60° C. over the course of about 4 hours,
   thereby producing granular resistant starch.
16. A method according to claim 15, wherein steps (c) and (d) are repeated sequentially at least once.
17. Aqueous granular resistant starch produced by a process which causes native starch granules to swell but not rupture and wherein the starch has an average viscosity lower than the average viscosity of resistant starch produced by a process in which the starch granules are ruptured.
18. A food or beverage formulation comprising the aqueous granular resistant starch of claim 17.
19. A food or beverage formulation according to claim 18, wherein the food or beverage formulation is selected from the group consisting of cookies, breads, cakes, pies, noodles, fudge, brownies, low-fat margarine, snack dips, sour cream, mayonnaise, cream cheese, spreads, yogurt, milkshakes, ice cream, frozen desserts, crackers, graham crackers, pretzels, extruded cereals and extruded snacks.
20. A food or beverage formulation which is a source of slow-released glucose comprising the aqueous granular resistant starch of claim 17.
21. A method for producing granular resistant starch, comprising the steps of:
   a) heating an aqueous slurry of native starch having a moisture content of from about 100% to about 600% starch weight under conditions appropriate for swelling of the native starch granules therein without causing rupture of said native starch granules;

b) debranching the starch product of step (a); and c) maintaining the debranched starch product of step (b) at an appropriate temperature and for an appropriate time to cause the starch product to retrograde, thereby producing granular resistant starch.

22. Granular resistant starch produced by the method of claim 21.

23. A method according to claim 21, wherein the moisture content is from about 270% to about 500% starch weight.

24. Aqueous granular resistant starch having a moisture content of from about 100% to about 600% starch weight and having an average viscosity lower than the average viscosity of resistant starch produced by a process in which the starch granules are ruptured.

* * * * *